United States Patent [19]

Hung

[11] Patent Number: 5,015,790

[45] Date of Patent: May 14, 1991

[54] 1,1,2-TRIFLUORO-6-IODO-1-HEXENE, 1,1,2-TRIFLUORO-1,5-HEXADIENE, AND PROCESSES THEREFORE

[75] Inventor: Ming-Hong Hung, Wilmington, Del.

[73] Assignee: E. I. Du Pont de Nemours and Company, Wilmington, Del.

[21] Appl. No.: 450,257

[22] Filed: Dec. 13, 1989

[51] Int. Cl.$^5$ .................. C07C 17/28; C07C 17/74; C07C 21/18

[52] U.S. Cl. .................. 570/126; 570/125; 570/139; 570/155; 570/156; 570/157

[58] Field of Search .............. 570/157, 125, 155, 156, 570/139, 126

[56] References Cited

U.S. PATENT DOCUMENTS

| | | | |
|---|---|---|---|
| 2,686,207 | 8/1954 | Crane et al. | 570/157 |
| 2,750,431 | 6/1956 | Tarrant et al. | 570/126 |
| 2,972,630 | 2/1961 | Tiers | 570/125 |
| 3,016,407 | 1/1962 | Brace | 570/139 |
| 3,083,238 | 3/1963 | Hauptschein et al. | 570/139 |
| 3,631,115 | 12/1971 | Nakagawa et al. | 570/139 |

FOREIGN PATENT DOCUMENTS

| | | | |
|---|---|---|---|
| 576707 | 5/1959 | Canada | 570/139 |
| 865858 | 4/1961 | United Kingdom | 570/139 |

OTHER PUBLICATIONS

Park et al., "J. Am. Chem. Soc.", vol. 78, pp. 59–62 (1956).

J. D. Park et al., J. Am. Chem. Soc., 78, 59 (1956).

H.-G. Viehe, Chemische Berichte, 97, 598 (1964), with translation.

*Primary Examiner*—J. E. Evans

[57] ABSTRACT

Fluorine-containing iodo-substituted 1-hexenes, their preparation by the addition of two moles of ethylene to fluorine-containing iodo olefins, and their dehydroiodination to fluorine-containing 1,5-dienes are disclosed.

10 Claims, No Drawings

1,1,2-TRIFLUORO-6-IODO-1-HEXENE, 1,1,2-TRIFLUORO-1,5-HEXADIENE, AND PROCESSES THEREFORE

FIELD OF THE INVENTION

This invention relates to novel, fluorine-containing iodo- substituted 1-hexenes, novel, fluorine-containing 1,5-dienes, and to methods of preparation for these compounds that involve the addition of two moles of ethylene to fluorine-containing iodo olefins, and the dehydroiodination of the resulting addition product, respectively.

BACKGROUND

J. D. Park et al., J. Am. Chem. Soc, 78, 59 (1956) disclose the addition of one mole of various olefinic compounds, including ethylene, to trifluoroiodoethene to form 1 plus 1 adducts (butenes) in which, in the case where ethylene is the added olefin, a β-iodoethyl group is bound to the trifluoroethene at the point at which the iodine was originally bound. There is no disclosure nor suggestion that more than one molecule of olefin can add to one molecule of trifluoroiodoethene, i.e., there is no suggestion of a 2 plus 1 adduct. This same reference discloses the dehydroiodination of the above 1 plus 1 adducts to form fluorine-substituted butadienes. There is no disclosure nor suggestion that this reaction would take place with 2 plus 1 adducts to yield a fluorine-substituted hexadiene.

H.-G. Viehe, Chemische Berichte, 97, 598(1964) discloses the reaction of ethylene with 2-fluoro-1-iodoethylene to yield the 1 plus 1 adduct, 1-fluoro-4-iodo-1-butene. There is no disclosure nor suggestion that more than one molecule of ethylene can add to one molecule of the iodo olefin, i.e., there is no suggestion of a 2 plus 1 adduct. It is also disclosed that dehydroiodination of the fluoroiodobutene gave 1-fluoro-1,3-butadiene. There is no disclosure nor suggestion that this reaction would take place with 2 plus 1 adducts to yield a fluorine-substituted hexadiene.

It is therefore an object of the present invention to provide novel fluorine-containing iodo hexenes.

It is a further object of the present invention to provide a novel process for the preparation of these compounds involving the telomerization of a fluorine-containing iodo-substituted olefin with excess ethylene to yield the 2 plus 1 adduct.

It is a further object of the present invention to provide novel fluorine-containing dienes and their preparation by dehydroiodination of the above 2 plus 1 adducts.

SUMMARY OF THE INVENTION

This invention provides compounds represented by formula (I)

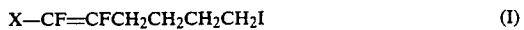

X—CF=CFCH$_2$CH$_2$CH$_2$CH$_2$I     (I)

wherein X may be F or C$_n$F$_{2n+1}$, and n is an integer from about 1 to 10.

This invention also provides a process for the preparation of the compounds represented by formula (I)

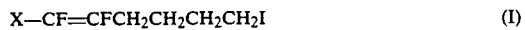

X—CF=CFCH$_2$CH$_2$CH$_2$CH$_2$I     (I)

wherein X is defined as above, comprising contacting an iododifluoroethylene represented by the formula X—CF=CFI, where X is defined as above, with ethylene under telomerization conditions.

This invention also provides fluorine-containing 1,5-diene compounds represented by formula (II)

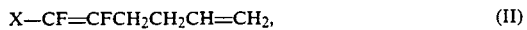

X—CF=CFCH$_2$CH$_2$CH=CH$_2$,     (II)

where X is defined as above for formula (I).

DETAILED DESCRIPTION OF THE INVENTION

The invention provides compounds represented by formula (I)

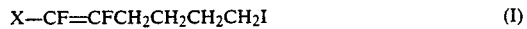

X—CF=CFCH$_2$CH$_2$CH$_2$CH$_2$I     (I)

wherein X may represent the fluoro group, F, or it may represent a perfluoroalkyl group, C$_n$F$_{2n+1}$, where n is an integer from 1 to about 10.

A second aspect of this invention is a process for the preparation of the above compounds of formula (I). These compounds are prepared by the reaction of a substituted iododifluoroethylene represented by the formula X—CF=CFI, where X is defined as above, with ethylene under telomerization conditions.

The simplest member of this series of compounds is that wherein X is F. In this case, the fluorinated starting material is iodotrifluoroethylene, and the product, after the addition of 2 moles of ethylene, is 6-iodo-1,1,2-trifluoro-1-hexene, CF$_2$=CFCH$_2$CH$_2$CH$_2$CH$_2$I.

These compounds have utility as intermediates in the synthesis of fluorine-containing organic molecules, especially as intermediates in the synthesis of the novel fluorine-containing dienes, X—CF=CFCH$_2$CH$_2$CH=CH$_2$. The compounds also have utility as monomers in the preparation of functionalized, that is, iodine-substituted, fluorine-containing polymers or copolymers.

In the reaction of the substituted iododifluoroethylene represented by the formula X—CF=CFI, where X is defined as above, with ethylene, it is necessary to operate with at least two moles of ethylene per mole of substituted iododifluoroethylene. It is preferable to operate with an excess of ethylene. It is preferable to use from about 2.5 to about 30 or more moles of ethylene per mole of substituted iododifluoroethylene.

The reaction of the substituted iododifluoroethylene with ethylene is carried out at an elevated temperature, preferably at from about 180° C. to about 250° C. The most preferred temperature is about 200° C. The reaction is usually carried out over about 10 to about 24 hours. The preferred reaction time is from about 20 to about 24 hours.

The ethylene reaction is carried out in a sealed vessel with elevated pressures. The pressure of the reaction is not, however, critical. The pressure depends predominantly on the amount of ethylene employed. Pressures of up to about 3750 psig, or more, are encountered.

It is advantageous to include a free radical inhibitor in the reaction of the substituted iododifluoroethylene with ethylene in order to control ethylene homopolymerization. The free radical inhibitors are those known in the art for to be useful for this purpose. In the examples attached to illustrate this invention d-limonene was employed.

The reaction is carried out without a source of radiation. The presence of a catalyst is not required. It is preferred to carry out the reaction with agitation.

Upon completion of the reaction period, the sealed vessel is cooled, excess ethylene is separated, and the desired product is collected and purified by means customary in the art.

The fluorine-containing iodohexenes, once obtained, are converted to fluorine-containing 1,5-diene compounds by dehydrohalogenation. A preferred method of dehydrohalogenation is carried out in aqueous suspension in the presence of a strong water-soluble inorganic base and a phase transfer catalyst. Separation of the organic product layer, followed by known-method purification affords the fluorine-containing 1,5-diene.

These compounds, representing a third aspect of the present invention, are denoted by formula (II):

$$X-CF=CFCH_2CH_2CH=CH_2 \qquad (II)$$

wherein X may represent the fluoro group, F, or it may represent a perfluoroalkyl group, $C_nF_{2n+1}$, where n is an integer from 1 to about 10.

The simplest member of the series of fluorine-containing 1,5-dienes provided by this invention, where X=F, is 1,1,2-trifluoro-1,5-hexadiene, $CF_2=CFCH_2CH_2CH=CH_2$.

These compounds have utility as intermediates in the synthesis of fluorine-containing organic molecules, especially as monomers in the preparation of fluorine-containing polymers or copolymers.

EXAMPLES

In the examples below, all temperatures are in degrees centigrade. The ethylene and d-limonene were purchased materials. The iodotrifluoroethylene was purchased from PCR Corporation. The ethylene reactions were carried out in pressure tubes manufactured from stainless steel or Hastalloy ® C. NMR spectra were recorded on a General Electric - QE300 instrument.

EXAMPLE 1

Preparation of 6-iodo-1,1,2-trifluoro-1-hexene, $CF_2=CFCH_2CH_2CH_2CH_2I$

To a 1400mL shaker tube were charged iodotrifluoroethylene (71.3 g, 0.343 mole) and d-limonene (1.7 g). The tube was cooled and evacuated. Ethylene gas (240 g, 8.57 mole) was charged; the tube was sealed and heated slowly, over approximately 18 hours, with agitation, to 200° C., and maintained at this temperature for 24 hours. The tube was then cooled, volatiles were vented, and the crude product was distilled to give a colorless oil, boiling point 58° C./2.5 mmHg. H-1 NMR (CDCl3): δ3.22 (m, 2H), 2.02 to 2.60 (m, 6H); F-19 NMR (CDC13): -103.5, 104.6 (2s, br, 1F), -114.7, -115.8 (2s, br, 1F), -164.1 (s, br, 1F).

EXAMPLE 2

Preparation of 6-iodo-1,1,2-trifluoro-1-hexene, $CF_2=CFCH_2CH_2CH_2CH_2I$

To a 240mL shaker tube were charged iodotrifluoroethylene (20.8 g, 0.100 mole) and d-limonene (0.4 g). The tube was cooled and evacuated. Ethylene gas (28 g, 1.0 mole) was charged; the tube was sealed and heated slowly, with agitation, to 250° C., and maintained at this temperature for 10 hours. The tube was then cooled, volatiles were vented, and the product was recovered from the tube. After combination with crude product from a similar preparation (differing in amount of d-limonene —0.5 g, amount of ethylene—56 g, and reaction temperature, 200° C.) and purification by distillation, a total of 36.0 g (34.1% yield for the two preparations) were obtained; boiling point 58° C./2.0-2.5 mmHg. Small amounts of compounds containing only one ethylene unit, and compounds containing three and four units of ethylene were also present.

EXAMPLE 3

Preparation of 1,1,2-trifluoro-1,5-hexadiene, $CF_2=CFCH_2CH_2CH=CH_2$

6-Iodo-1,1,2-trifluoro-1-hexene, obtained as above (52.8 g, 0.2 mole) was mixed with 10 M aqueous potassium hydroxide solution (125 mL, 1.25 mole) and 14.4 g of a 60% by weight aqueous solution of a phase transfer catalyst [benzyldodecyl-bis-(2-hydroxy-propyl)ammonium chloride] in a round bottom flask. The mixture was stirred for 24 hours at room temperature. The top organic layer was separated, washed with water, and distilled to give 20 g of the title product (73.5% yield) as a clear colorless liquid; boiling point 50° C./200 mm Hg. H-1 NMR (CDCl3): δ6.00 (m, 1H), 5.52 (m, 2H), 2.54 (m, 1H), 2.30 (m, 1H), 2.20 (m, 2H); F-19 NMR (CDC13): -100.8, -101.9 (2m, 1F), -115.4, -116.5 (2m, 1F), -161.8 (m, 1F).

What is claimed is:

1. A compound having the formula (I):

$$X-CF=CFCH_2CH_2CH_2CH_2I \qquad (I)$$

wherein X is F or $C_nF_{2n+1}$, and n is an integer from 1 to about 10.

2. The compound of claim 1 which is 6-iodo-1,1,2-trifluoro-1-hexene.

3. A compound having the formula (II):

$$X-CF=CFCH_2CHCH=CH_2, \qquad (II)$$

wherein X is F or $C_nF_{2n+1}$, and n is an integer from 1 to about 10.

4. The compound of claim 3 which is 1,1,2-trifluoro-1,5-hexadiene.

5. A process for the preparation of a compound of formula (I):

$$X-CF=CFCH2CH2CH2CH2I \qquad (I)$$

wherein X is F or $C_nF_{2n+1}$, and n is an integer from 1 to about 10, comprising contacting at least one mole of an iododifluoroolefin of formula X—CF=CFI, wherein X is defined as in formula (I), with at least two moles of ethylene under telomerization conditions.

6. The process of claim 5 conducted at a temperature of from about 180° C. to about 250° C. under elevated pressure.

7. The process of claim 5 wherein a free radical inhibitor is added to the reactants to control ethylene homopolymerization.

8. A process for the preparation of a compound of formula (II):

$$X-CF=CFCH_2CHCH=CH_2, \qquad (II)$$

wherein X is F or $C_nF_{2n+1}$, and n is an integer from 1 to about 10, comprising:

(a) contacting an iododifluoroolefin of formula X—CF=CFI, wherein X is defined as in formula (II) above, with an excess of ethylene under telomerization conditions to yield a compound of formula (I):

(I)

wherein X is defined as in formula (II) above; and
(b) dehydrohalogenating said compound of formula (I) to yield a compound of formula (II).

9. The process of claim 10 wherein in step (a) a free radical inhibitor is added to the reactants to control ethylene homopolymerization.

10. The process of claim 8 wherein in step (b) a strong inorganic base and phase transfer catalyst are added to the reactants.

* * * * *